(12) United States Patent
Tsai et al.

(10) Patent No.: US 10,188,684 B2
(45) Date of Patent: Jan. 29, 2019

(54) METHOD FOR PREVENTING OR TREATING FUNCTIONAL GASTROINTESTINAL DISORDER BY LACTIC ACID BACTERIUM

(71) Applicant: National Yang-Ming University, Taipei (TW)

(72) Inventors: Ying-Chieh Tsai, Taipei (TW); Jian-Fu Liao, Taipei (TW); Chih-Chieh Hsu, Taipei (TW)

(73) Assignee: National Yang-Ming University, Taipei (TW)

( * ) Notice: Subject to any disclaimer, the term of this patent is extended or adjusted under 35 U.S.C. 154(b) by 81 days.

(21) Appl. No.: 14/690,502

(22) Filed: Apr. 20, 2015

(65) Prior Publication Data

US 2016/0303173 A1    Oct. 20, 2016

(51) Int. Cl.
A61K 35/00    (2006.01)
A61K 35/747   (2015.01)

(52) U.S. Cl.
CPC ................... *A61K 35/747* (2013.01)

(58) Field of Classification Search
CPC ....................................................... C12R 1/25
See application file for complete search history.

(56) References Cited

U.S. PATENT DOCUMENTS

2012/0282675 A1* 11/2012 Kim ................. A61K 35/747
                                                      435/252.9
2013/0101566 A1*  4/2013 Espadaler Mazo .... A61K 35/74
                                                      424/93.21

OTHER PUBLICATIONS

Chao et al, Diversity of lactic acid bacteria in suan-tsai and fu-tsai, traditional fermented mustard products of Taiwan, International Journal of Food Microbiology, 135 (2009) 203-210.*
U.S. Appl. No. 14/259,442.*
Ducrotte et al., World J Gastroenterol Aug. 14, 2012 18 (30): 4012-4018.*

Bouin et al., "Rectal Distention Testing in Patients with Irritable Bowel Syndrome: Sensitivity, Specificity, and Predictive Values of Pain Sensory Thresholds," *Gastroenterology*, 122:1771-1777 (2002).
Chen et al., "Visceral Hypersensitivity in Non-Erosive Reflux Disease: Neurogenic Overwhelming in Esophagus?" *Dig. Dis. Sci.*, 58:2131-2132 (2013).
Collins, "Translating symptoms into mechanisms: functional GI disorders," *Adv. Physiol. Educ.*, 31:329-331 (2007).
Dalton, "What is a Functional GI Disorder?" UNC Center for Functional GI & Motility Disorders, 3 pages.
Drossman, "The Functional Gastrointestinal Disorders and the Rome III Process," *Gastroenterology*, 130:1377-1390 (2006).
Keohane and Quigley, "Functional dyspepsia: the role of visceral hypersensitivity in its pathogenesis," *World J. Gastroenterol.*, 12(17):2672-2676 (2006).
Moshiree et al., "Central sensitisation in visceral pain disorders," *Gut*, 55:905-908 (2006).
Neri et al., "Effect of Colic Vein Ligature in Rats with Loperamide-Induced Constipation," *J. Biomed. Biotech.*, vol. 2012, article ID 896162, 5 pages (2012).
Serafini et al., "Kefir fermented milk and kefiran promote growth of *Bifidobacterium bifidum* PRL2010 and modulate its gene expression," *Intl. J. Food Microbiol.*, 178:50-59 (2014).
Wang et al., "Alternation of substance P-containing neural pathways in a rat model of irritable bowel syndrome with rectal distension," *Chinese J. Digestive Diseases*, 7:211-218 (2006).

\* cited by examiner

*Primary Examiner* — Ruth A Davis
(74) *Attorney, Agent, or Firm* — McCarter & English, LLP; Yu Lu

(57) ABSTRACT

The present invention provides a method for preventing or treating a functional gastrointestinal disorder in a subject in need thereof that includes a step of administering a composition, wherein the composition includes an effective amount of *Lactobacillus plantarum* subsp. *plantarum* PS128 and a carrier. The present invention further provides a method for preventing or treating visceral hypersensitivity in a subject in need thereof that includes a step of administering a composition, wherein the composition includes an effective amount of *Lactobacillus plantarum* subsp. *plantarum* PS128 and a carrier. Moreover, the present invention provides a method for preventing or treating functional abdominal pain, irritable bowel syndrome or constipation in a subject in need thereof that includes a step of administering a composition, wherein the composition includes an effective amount of *Lactobacillus plantarum* subsp. *plantarum* PS128 and a carrier.

17 Claims, 3 Drawing Sheets

Specification includes a Sequence Listing.

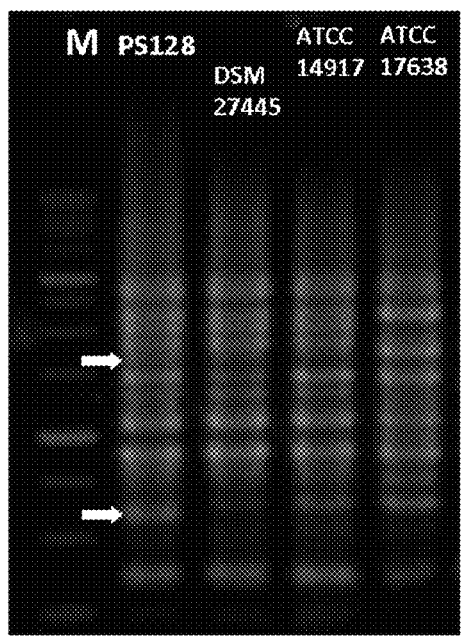
FIG. 1
FIG. 2A
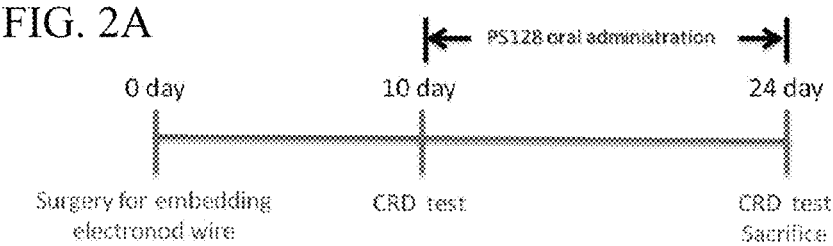
FIG. 2B
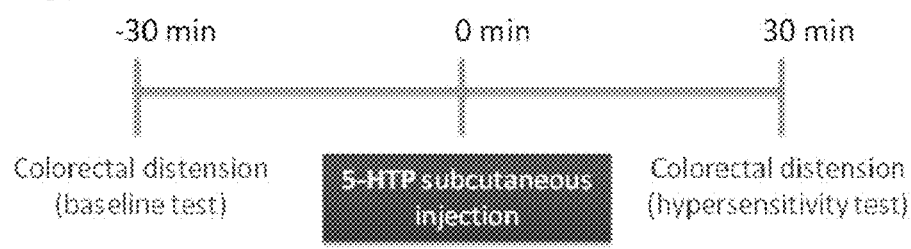

METHOD FOR PREVENTING OR TREATING FUNCTIONAL GASTROINTESTINAL DISORDER BY LACTIC ACID BACTERIUM

BACKGROUND OF THE INVENTION

1. Field of the Invention

This invention relates to methods for preventing or treating functional gastrointestinal disorder, and relates particularly to a method for preventing or treating functional abdominal pain, irritable bowel syndrome or constipation in a subject.

2. Description of Related Art

Functional gastrointestinal disorders (FGIDs) are the most common problem in gastroenterological practice. These occur as a result of abnormal functioning of the GI tract, and they are defined by chronic abdominal symptom complexes, such as abdominal pain, diarrhea, constipation, and bloating. According to Rome III criteria, more than 20 functional GI disorders have been identified. Common FGIDs include, but are not limited to functional abdominal pain, irritable bowel syndrome (IBS), constipation, functional diarrhea and functional dyspepsia.

Irritable bowel syndrome is a chronic functional gastrointestinal disorder. About 4-30% people worldwide suffer from IBS. IBS has been characterized by two major symptoms: abdominal pain (chronic pain) and bowel habits alteration. According to the predominant symptom, IBS can be classified into four subgroups: IBS with diarrhea (IBS-D), IBS with constipation (IBS-C), mixed IBS (IBS-M), and un-subtyped IBS (IBS-U). In IBS patients, about 30% patients suffer from IBS after gastrointestinal inflammation, and those belong to post-infectious/inflammatory IBS. In addition, the major factor in motivating patients to seek healthcare and causing a significant reduction in quality of life is abdominal pain, which is associated with visceral hypersensitivity (VH). Visceral hypersensitivity is considered to be one of the main mechanisms causing functional gastrointestinal disorders. Moreover, recent studies show that visceral hypersensitivity is highly specific for IBS.

Visceral hypersensitivity is defined as the increased intensity of sensations and the lowered thresholds for visceral pain in patients. The persistent VH is associated with neuronal sensitization, which manifests as an increase in neuronal excitability. Neurotransmitters, such as serotonin (5-hydroxytryptamine, 5-HT), play important roles in neuronal sensitization. Serotonin is a monoamine neuron transmitter. Previous study have shown that awake rats with subcutaneous injection of 5-hydroxytryptophan (5-HTP), a precursor of serotonin, induced VH. The predominant site of serotonin synthesis and storage is the enterochromaffin cells of the intestinal mucosa. Serotonin released from enterochromaffin cells activates neural reflexes associated with intestinal secretion, motility, and sensation. According to clinical studies, patients with IBS are usually accompanied with abnormality of serotonin metabolism. Furthermore, serotonin receptor antagonists have been used widely as a therapeutic drug, indicating that the pathology of IBS is associated with serotonin.

Lowered pain threshold in a rectal distention test, representing visceral hypersensitivity, is a hallmark of IBS patients. In animal studies, colorectal pain threshold can be monitored by electromyography (EMG) signals responded to a barostat distension, and a higher response of EMG signal represents a higher sensitivity to pain. In addition to VH, an increased expression of substance P in the spinal cord has also been demonstrated as a biomarker representing visceral pain sensation during colorectal distension in an IBS rat model.

There are various therapeutic methods to ameliorate symptoms of IBS, including as serotonin receptor antagonists, antidepressant drugs, prokinetics drugs, antispasmodics drugs and probiotics. Probiotics are live microorganisms which, when administered in adequate amounts, confer a health benefit on the host. Due to the absence of pharmacological side effects, probiotics appear to be a potential method for the treatment of IBS. Besides, specific probiotics have been described to confer beneficial effects on constipation symptoms. Probiotics can make host gain healthy benefit via keeping gut flora balance, strengthening mucosal barrier function and modulating immune system. There are lots of evidences indicating that probiotics can act as a therapeutic way of diseases, including infectious diseases, allergy, cancer and necrotising enterocolitis. It is worth to further research the use of probiotics in treating functional gastrointestinal disorders.

Constipation, a worldwide functional gastrointestinal disorder, is defined as infrequent or difficult passage of stool. Constipation has many causes, including chemical compounds, dietary habits, intestinal flora composition, pregnancy, and psychological stress. Although many types of purgative drugs have been identified, most of these drugs have potentially adverse side effects such as inducing tolerance, melanosis coli, or cathartic colon. There is a dysbiosis of the intestinal flora in patients with constipation, which could be improved by consumption of probiotics. Furthermore, probiotic bacteria, especially lactobacilli and bifidobacteria, may lower the pH of the colon, producing lactic acid, acetic acid, and others. A lower pH tends to increase colonic peristalsis and, in consequence, decrease colonic transit time, with a beneficial effect in the treatment of constipation symptoms.

Many studies had show that production and manufacturing methods and the food carrier may influence the properties of probiotic strains, and have an impact on the outcome of clinical intervention studies. Here, we identified a lactic acid bacterium strain under specific manufacturing process (artificial cultured) showed the potential that preventing or treating functional gastrointestinal disorder.

SUMMARY OF THE INVENTION

The inventors discover that a lactic acid bacterium, *Lactobacillus plantarum* subsp. *plantarum* PS128 (hereinafter sometimes referred to as PS128), is useful for preventing or treating FGIDs, especially useful for preventing or treating visceral hypersensitivity.

In an aspect of the present invention, a method for preventing or treating a functional gastrointestinal disorder in a subject in need thereof is provided. In accordance with the present invention, the method comprises administering a composition, wherein the composition comprises an effective amount of a *Lactobacillus plantarum* subsp. *plantarum* PS128, which is deposited under DSMZ Accession No. DSM 28632, and a carrier. Preferably, the composition is orally administrated.

In one embodiment of the present invention, the functional gastrointestinal disorder is selected from the group consisting of functional abdominal pain, irritable bowel syndrome, constipation, functional diarrhea and functional dyspepsia. In a preferable embodiment, the functional gastrointestinal disorder is functional abdominal pain, irritable bowel syndrome or constipation.

In another aspect of the present invention, a method for preventing or treating visceral hypersensitivity in a subject in need thereof is provided. In accordance with the present invention, the method comprises administering a composition, wherein the composition comprises an effective amount of Lactobacillus plantarum subsp. plantarum PS128, which is deposited under DSMZ Accession No. DSM 28632, and a carrier. Preferably, the composition is orally administered to the subject.

In one embodiment of the present invention, the visceral hypersensitivity is associated with a functional gastrointestinal disorder and the functional gastrointestinal disorder is one selected from the group consisting of functional abdominal pain, irritable bowel syndrome, functional constipation, functional diarrhea and functional dyspepsia. In a preferable embodiment, the functional gastrointestinal disorder is functional abdominal pain, irritable bowel syndrome or constipation.

In another aspect of the present invention, a method for preventing or treating functional abdominal pain, irritable bowel syndrome or constipation in a subject in need thereof is provided. In accordance with the present invention, the method comprises administering a composition, wherein the composition comprises an effective amount of Lactobacillus plantarum subsp. plantarum PS128, which is deposited under DSMZ Accession No. DSM 28632, and a carrier. Preferably, the composition is orally administered to the subject.

In a further embodiment, after the administration of the composition, a level of a biomarker of pain sensation is statistically significantly decreased in the subject. Preferably, the biomarker is substance P.

In a further embodiment, after the administration of the composition, an electromyography signal is statistically significantly decreased in the subject.

In one embodiment of the present invention, the carrier is a physiologically acceptable excipient or diluent. The examples of the physiologically acceptable excipient or diluent include, but are not limited to, lactose, starch, dextrin, cyclodextrin, sodium carboxymethyl starch, carboxylated starch propionate, microcrystalline cellulose, carboxymethyl cellulose, maltodextrin and magnesium stearate.

BRIEF DESCRIPTION OF THE DRAWINGS

FIG. 1 is an electrophoresis photograph showing the ERIC-PCR profiles of Lactobacillus plantarum strains, wherein M represents DNA ladder; DSM 27445 represents Lactobacillus plantarum subsp. plantarum; ATCC 14917[T] represents Lactobacillus plantarum subsp. plantarum; and ATCC 17638[T] represents Lactobacillus plantarum subsp. argentoratensis.

FIG. 2A shows an experimental timeline for assessing the effect of PS128 on 5-HTP-induced visceral hypersensitivity and FIG. 2B shows the experimental procedures of visceral hypersensitivity test.

DETAILED DESCRIPTION OF THE INVENTION

Figure 3A:
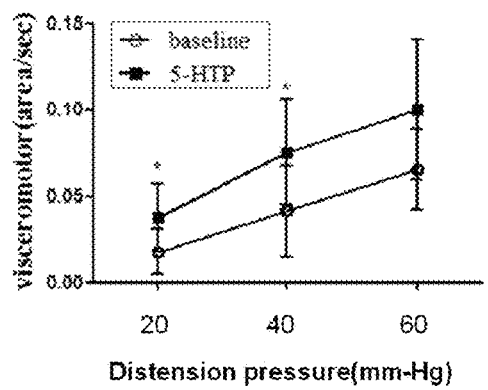
FIGS. 3A-3C show electromyography (EMG) signals responded to CRD stimulation (n=8, $*p<0.05$, $p<0.01$, $*p<0.0001$, baseline vs. 5-HTP; Student's t test).

The following specific examples are used for illustrating the present invention. A person skilled in the art can easily conceive the other advantages and effects of the present invention. The present invention can also be implemented by different specific cases be enacted or application, the details of the instructions can also be based on different perspectives and applications in various modifications and changes do not depart from the spirit of the creation.

Many examples have been used to illustrate the present invention. The examples sited below should not be taken as a limit to the scope of the invention.

EXAMPLES

Example 1

Isolation of Lactobacillus plantarum subsp. plantarum PS128 and Discrimination of the Novel Bacterial Strains Using ERIC-PCR Profiles Lactobacillus plantarum subsp. plantarum PS128 (hereinafter referred to PS128) was isolated from fu-tsai, traditional fermented mustard products of Taiwan.

ERIC-PCR was conducted to further distinguish the subspecies of bacteria with high sequence similarity.

The ERIC-PCR profile of Lactobacillus plantarum strains was carried out under the condition indicated in Table 1 and Table 2. DNAs extracted from PS128 and three Lactobacillus plantarum strains were used as templates. The obtained amplification products were electrophoresed and the patterns were compared as shown in FIG. 1, wherein the primers represented by SEQ ID NO: 1 and SEQ ID NO: 2 were used.

```
ERIC1R:
                                      SEQ ID NO: 1
(5'-ATGTAAGCTCCTGGGGATTCAC-3')

ERIC2:
                                      SEQ ID NO: 2
(5'-AAGTAAGTGACTGGGGTGAGCG-3')
```

TABLE 1

| Composition of the PCR reaction solution (25 µl per PCR tube) | |
|---|---|
| Component | Volume |
| ddH$_2$O | 16.3 µl |
| 10X PCR Buffer | 2.5 µl |
| dNTP | 2.0 µl |
| MgCl$_2$ (25 mM) | 1.0 µl |
| primer (GTG)$_5$ (10 µM) | 2.0 µl |
| rTaq polymerase | 0.2 µl |
| DNA template (10 µM) | 1.0 µl |

TABLE 2

| PCR Conditions | | |
|---|---|---|
| Temperature | Time | Cycle |
| 94° C. | 5 min | |
| 94° C. | 30 sec | 35 cycles |

TABLE 2-continued

PCR Conditions

| Temperature | Time | Cycle |
|---|---|---|
| 45° C. | 1 min | |
| 65° C. | 6 min | |
| 65° C. | 10 min | |

As shown in FIG. 1, Lane M represents DNA ladder (250-10000 bp); DSM 27445 represents *Lactobacillus plantarum* subsp. *plantarum*; ATCC 14917[T] represents *Lactobacillus plantarum* subsp. *plantarum*; and ATCC 17638[T] represents *Lactobacillus plantarum* subsp. *argentoratensis*.

As indicated by white arrows, the bands of PS128 are unique in position among those of DSM 27445, ATCC 14917[T] or ATCC 17638[T] and hence the result in FIG. 1 shows that even though PS128, DSM 227445 and ATCC 14917[T] all belong to *Lactobacillus plantarum* subsp. *plantarum*, they are still different bacterial strains. Consequently, PS128 represented a new strain of *Lactobacillus plantarum* subsp. *plantarum*.

*Lactobacillus plantarum* subsp. *plantarum* PS128 has been deposited under Budapest Treaty at Leibniz Institute DSMZ-German Collection of Microorganisms and Cell Cultures (Inhoffenstr. 7 B, D-38124 Braunschweig, Germany) on Mar. 31, 2014 and has been given the DSMZ Accession No. DSM 28632 by the International Depositary Authority. This biological material was subjected to the viability test and passed.

Example 2

Analytical Profile Index (API) Typing

Sugar utilization for PS128 used in the present invention was investigated using API 50 CHL kit (bioMerieux, France), and the results are shown in Table 3. The fermentation test indicates that PS128 harbor a biochemical property similar to *Lactobacillus plantarum* subsp. *plantarum*.

TABLE 3

Results of Fermentation Test[a]

| Carbohydrates Substrate Strips | PS128 |
|---|---|
| CONTROL | − |
| Glycerol | − |
| Erythritol | − |
| D-Arabinose | − |
| L-Arabinose | + |
| D-Ribose | + |
| D-Xylose | + |
| L-Xylose | − |
| D-Adonitol | − |
| Methyl-β-D-Xylopyranoside | − |
| D-Galactose | + |
| D-Glucose | + |
| D-Fructose | + |
| D-Mannose | + |
| L-Sorbose | − |
| L-Rhamnose | + |
| Dulcitol | − |
| Inositol | − |
| D-Mannitol | + |
| D-Sorbitol | + |
| Methyl-α-D-mannopyranoside | + |
| Methyl-α-D-glucopyranoside | − |
| N-Acetyl glucosamine | + |

TABLE 3-continued

Results of Fermentation Test[a]

| Carbohydrates Substrate Strips | PS128 |
|---|---|
| Amygdalin | + |
| Arbutin | + |
| Esculin ferric citrate | + |
| Salicin | + |
| D-Cellobiose | + |
| D-Maltose | + |
| D-Lactose (bovine origin) | + |
| D-Melibiose | + |
| D-Saccharose (sucrose) | + |
| D-Trehalose | + |
| Inulin | + |
| D-Melezitose | + |
| D-Raffinose | + |
| Amidon (starch) | − |
| Glycogen | − |
| Xylitol | − |
| Gentiobiose | + |
| D-Turanose | + |
| D-Lyxose | − |
| D-Tagatose | + |
| D-Fucose | − |
| L-Fucose | − |
| D-Arabitol | − |
| L-Arabitol | − |
| Potassium gluconate | + |
| Potassium 2-ketogluconate | − |
| Potassium 5-ketogluconate | − |

[a]+, positive;
−, negative;

Example 3

Alternations of Visceral Hypersensitivity and Substance P Levels in Rats by *Lactobacillus plantarum* subsp. *plantarum* PS128

Previous study have shown that awake rats with subcutaneous injection of 5-hydroxytryptophan (5-HTP), a precursor of serotonin, induced VH. In this study, the 5-HTP-induced VH model was used to evaluate ameliorative effects of a probiotic strain, *Lactobacillus plantarum* subsp. *plantarum* PS128, on rats.

(1) Preparation of PS128

PS128 was inoculated in culture medium (10% skim milk, 1% yeast powder, 0.1% tween 80, and 2% glucose), cultured at 37° C. for 18 hrs and harvested by centrifugation. PS128 was embedded and lyophilized with protective agents (skim milk 1%, Sugar 2%, oligofructose 2%, maltodextrin 3%, and glycerol 2%) and excipients to a final concentration of $5 \times 10^9$ colony formation unit (CFU) per gram powder. PS128 powder was stored at −20° C. and was dissolved into $10^9$ CFU/mL in saline solution before animal treatment.

(2) Animals and Housing

Six to eight-week-old Male Sprague-Dawley (SD) rats (220 to 330 g) were purchased from National Laboratory Animal Center (NLAC, Taipei, Taiwan). The rats were housed under constant temperature and humidity with 12-h light-dark cycles, and were given free access to food and water. All animal experimental procedures were reviewed and approved by the Animal Management Committee, National Yang-Ming University.

(3) Experiment Procedure

Referring to FIG. 2A, rats at first were anesthetized with isoflurane for electrode implantation. After surgery for embedding electrode, rats were housed in single. On about 7-10 days after the surgery, rats were underwent colorectal distension (CRD) test for baseline and visceral hypersensitivity detection induced by 5-HTP injection. This test was designed to verify the 5-HTP-visceral hypersensitivity in awake male rats without bacteria administration. On day 10, rats were orally administered with PS128 (about $10^9$ CFU per day) or saline (200 μl per day) for two weeks followed by CRD experiment. After that, another CRD test would be processed to determine the effect of PS128 on VH. The CRD procedure with simultaneous electromyography (EMG) recording was performed. The area under the EMG curve (AUC) was calculated as a parameter. For detecting the protein level of substance P in spinal cord by western blotting, the rats were anesthetized with sodium pentobarbital (65 mg/kg, intraperitoneal injection) and perfused transcardially with normal saline. The L6-S1 spinal cord of rats responsible for abdominal sensation was isolated.

(4) Electrode Implantation

The rats were anesthetic with isoflurane. Electrodes made from Teflon-coated stainless steel wire (A-M systems Inc.) were implanted in the rat's abdominal external oblique muscle at least 7 days prior to experimentation. Electrodes were exteriorized onto the back of the neck.

(5) Colorectal Distension (CRD) Test

Colorectal distension (CRD) is a widely used and reproducible method for assessing visceral sensitivity. The measurement of electromyography signals is one of the evaluation items in CRD and is the most accurate quantitative test item.

Referring to FIG. 2B, CRD tests were processed before and after 5-HTP subcutaneous injection (5 mg/Kg) for determining 5-HTP-induced visceral hypersensitivity.

For the CRD test, rats were placed in plastic tunnels (6-cm diameter, 25-cm length). During 3 days for preceding the test, the rats were trained to the experimental conditions by placing them singly in the tunnel for 3 hours per day. The colorectal distension (CRD) balloon was composed of a latex glove finger (7 cm long) attached to a rectal catheter (Medtronic Inc.). The balloon was inflated and left overnight to help equilibrate the tension in its wall. The inflatable device was introduced through the anal canal completely into the rectum in conscious rats and secured to the tail base. The tube was then connected to a barostat (Medtronic Inc.). The colon was distended by inflating the balloon to the desired pressure (20, 40, or 60 mmHg) for 10-second intervals with 30-second intervals between distensions. Distensions were repeated 4 times for each experimental protocol with 5-minute intervals between each series. The response of CRD was record by an EMG device. The EMG signal analyses were processed by Spike 2 (Cambridge Electronic Design Limited) as visceromotor reflex (area/sec).

As shown in FIG. 3A, the visceromotor was calculated from the raw EMG signal and increases gradually in a pressure-dependent manner in every groups. Subcutaneous injection of 5-HTP significantly increased the EMG signal in response to CRD relative to the baseline signal in rats.

Figure 3B:
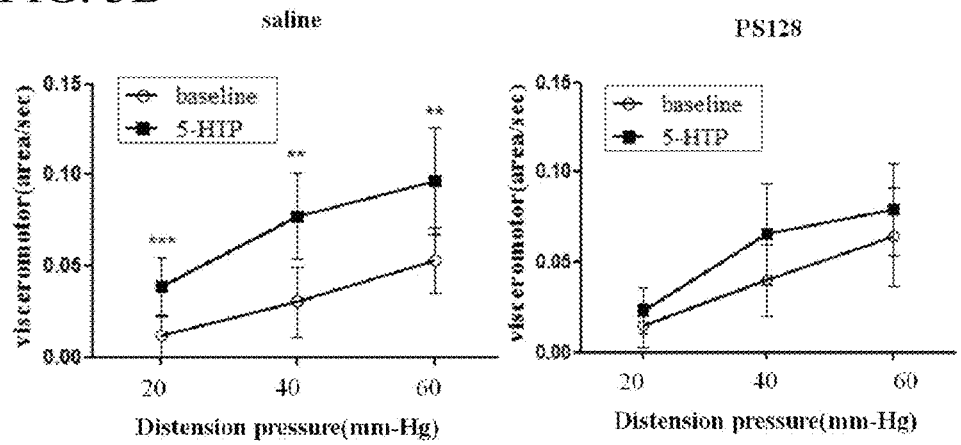

As shown in FIG. 3B, with two weeks administration of saline, the EMG signals were still elevated significantly after 5-HTP injection while rats with two weeks PS128 administration could inhibit the elevation of EMG signal induced by 5-HTP.

Furthermore, to confirm the effect of administration of PS128 on inhibiting the elevation of EMG signal, we calculated the difference of the elevation of EMG after 5-HTP injection between day 10 and day 24. The formula of EMG difference is shown below:

EMG difference=(The difference of the elevation of EMG after 5-HTP injection on day 24)−(The difference of the elevation of EMG after 5-HTP injection on day 10)

Figure 3C:
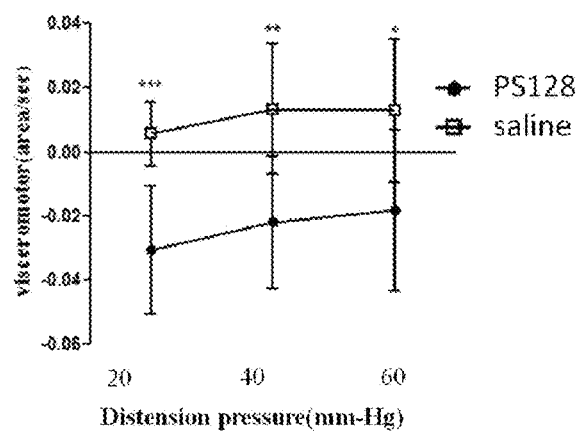

As shown in FIG. 3C, after saline administration, there was more elevation of EMG signal on day 24 compared with that on day 10 in all distension pressure stimulation. In PS128 group, however, there was lower elevation of the EMG signal on day 24 compared with that on day 10 in all distension pressure stimulation. These data indicated that PS128 had a potential to ameliorate VH induced by 5-HTP injection.

(6) Western Blotting

For confirming the effect of PS128 on spinal neuron peptide associated with pain sensation by western blotting, total proteins in the L6-S1 spinal cord tissue were extracted with commercial protein extraction kit (EC21 Inc.). The extractions were fractionated on 10% polyacrylamide gels and then transfer to polyvinylidene difluoride membranes (Roche Ltd.) electrophoretically, followed by blockage for 1 hour with blocking buffer, TBST containing 5% Skim milk, and incubated with the primary antiserum substance P (1:1000; GeneTex Inc.) in blocking buffer overnight at 4° C. After twice washed with TBST, membrane was incubated with goat anti-rat IgG-HRP (1:5000; Santa Cruz Biotechnology, Inc.) in blocking buffer. The antibody-protein complex was visualized by Immobilon™ Western Chemiluminescent HRP Substrate (Millipore Inc.) and detected by Luminescent Image Analyzer (FUJIFILM Holdings Corporation).

Figure 4:
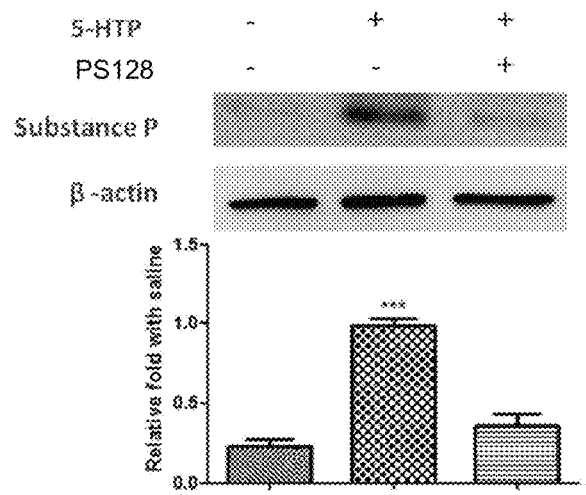
FIG. 4 shows the western blotting analysis of substance P level in L6-S1 spinal cord, which was isolated from a rat with or without PS128 administration (n=3, $***p<0.0001$; One way ANOVA test).

Substance P is a biomarker of pain sensation in the spinal cord of rats. It is suggested that an abnormal expression level of substance P involves in the pathogenesis of IBS. In addition, the substance P-containing neural pathway is considered as one of neural pathways which play a role in the regulation of the gastrointestinal function. As shown in FIG. 4, rats with two weeks saline oral administration were found high level substance P production in L6-S1 spinal cord after 5-HTP injection followed by CRD experiment, while control rats, without 5-HTP injection, had basal level production. Two weeks administration of PS128 inhibited the elevation of substance P production induced by 5-HTP injection. That is, with PS128 administration, the level of substance P was reversed almost to the level of rats without 5-HTP injection.

Example 4

Laxative Effect of PS128

Loperamide is an agonist of μ-opioid receptor, which inhibits endogenous acetylcholine release as a result of inhibitions of adenylcyclase via G protein in myenteric plexus. Loperamide is estimated to act directly on the intestinal nerve system to induce constipation and frequently used in constipation model mice.

Figure 5A:
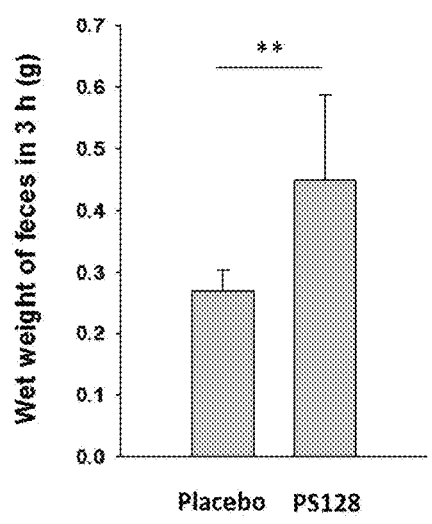
FIGS. 5A and 5B show the effects of orally administered PS128 on stool weight in normal (A) and experimental constipated (B) mice (data shown as the means±S.D., n=6, $**p<0.01$, $*p<0.05$ (unpaired t test)).
Figure 5B:
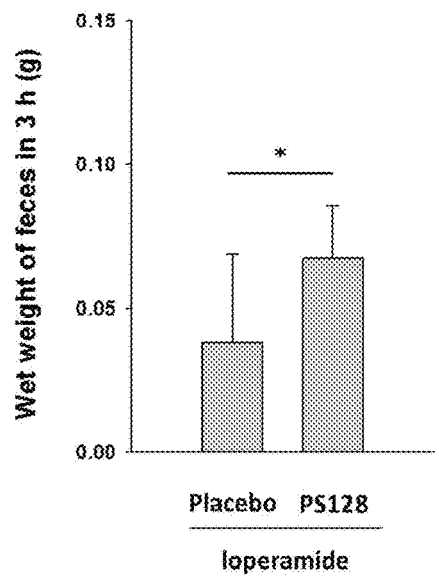

The laxative effect of PS128 on evacuating both normal and loperamide-induced constipated mice was further examined. Mice were orally administrated with placebo (0.2 mL saline/mouse/day) or PS128 ($10^9$ CFU in 0.2 mL saline/mouse/day). After 2 weeks, the wet weights of stools from each mouse were measured for 3 hrs. For experimental constipated mice, loperamide hydrochloride (5 mg/kg) was orally administrated, and after 30 minutes, the measurement was initiated and the wet weights of stools from each experimental constipated mouse were measured for 3 hrs. As shown in FIG. 5, the wet weights of stools of PS128 groups were significantly increased compared with those of the placebo groups, thereby suggesting the laxative effect of PS128. Those results suggest that PS128 has the potential of alleviating constipation.

Example 5

Statistical Analysis

Differences between experimental groups were analyzed with Prism version 6 (Prism, San Diego, Calif.). Student t test was used to analyze the difference of the EMG signals prior to CRD stimulation between two groups. One-way ANOVA was used to analyze the production of substance P detected by western blotting. Values are expressed as mean±SD. Differences were considered to be statistically significant at $p<0.05$.

The present invention finds that *Lactobacillus plantarum* subsp. *plantarum* PS128 exerts benefits on visceral hypersensitivity and constipation, and PS128 also eliminates the elevation of EMG signals and inhibits the elevated production of substance P in the spinal cord of rats after 5-HTP injection. Therefore, the method according to the present invention is useful for the prevention or treatment of a functional gastrointestinal disorder by administrating a composition which comprises a *Lactobacillus* strain PS128.

While some of the embodiments of the present invention have been described in detail in the above, it is, however, possible for those of ordinary skill in the art to make various modifications and changes to the particular embodiments shown without substantially departing from the teaching and advantages of the present invention. Such modifications and changes are encompassed in the spirit and scope of the present invention as set forth in the appended claim.

The references listed below and the DSMZ and ATCC numbers cited in the application are each incorporated by reference as if they were incorporated individually:

Chen, C L, "Visceral hypersensitivity in non-erosive reflux disease: neurogenic overwhelming in esophagus?" *Dig. Dis. Sci.*, 58(8):2131-2132 (2013).

Collins, S M, "Translating symptoms into mechanisms: functional GI disorders," *Adv. Physiol. Educ.*, 31(4):329-331 (2007).

Drossman, D A, "The functional gastrointestinal disorders and the Rome III process," *Gastroenterology*, 130(5):1377-90 (2006).

Keohane, J, Quigley, E M, "Functional dyspepsia: the role of visceral hypersensitivity in its pathogenesis," *World J. Gastroenterol.*, 7; 12(17):2672-2676 (2006).

Moshiree, B, Zhou, Q, Price, D D, Verne, G N, "Central sensitisation in visceral pain disorders," *Gut*, 55(7):905-908 (2006).

Bouin, M, Plourde, V, Boivin, M, Riberdy, M, Lupien, F, Laganiere, M, Verrier, P, Poitras, P, "Rectal distention testing in patients with irritable bowel syndrome: sensitivity, specificity, and predictive values of pain sensory thresholds," *Gastroenterology*, 122:1771-1777 (2002).

Wang, W. F., Yang, Y. S., Peng, L. H., and Sun, G, "Alternation of substance P-containing neural pathways in a rat model of irritable bowel syndrome with rectal distension," *Chin. J. Dig. Dis.*, 7(4):211-218 (2006).

Neri, F, Cavallari, G, Tsivian, M, Bianchi, E, Aldini, R, Cevenini, M, Guidetti, E, Piras, G L, Pariah, M, Nardo, B, "Effect of colic vein ligature in rats with loperamide-induced constipation," *J. Biomed. Biotechnol.*, 2012:896162, 5 pages (2012).

Fausta Serafini, Francesca Turroni, Patricia Ruas-Madiedo, Gabriele Andrea Lugli, Christian Milani, Sabrina Duranti, Nicole Zamboni, Francesca Bottacini, Douwe van Sinderen, Abelardo Margolles, Marco Ventura, "Kefir fermented milk and kefiran promote growth of *Bifidobacterium bifidum* PRL2010 and modulate its gene expression," *International Journal of Food Microbiology*, 178:50-59 (2014).

What is claimed is:

1. A method for treating a functional gastrointestinal disorder in a subject in need thereof, comprising administering a composition which comprises an effective amount of a *Lactobacillus plantarum* subsp. *plantarum* PS128 as the only active ingredient for treating the functional gastrointestinal disorder, which is deposited under DSMZ Accession No. DSM 28632, and a carrier, wherein the functional gastrointestinal disorder is selected from the group consisting of constipation, and functional dyspepsia.

2. The method according to claim 1, wherein the functional gastrointestinal disorder is constipation.

3. The method according to claim 1, wherein the composition is orally administrated to the subject.

4. The method according to claim 1, wherein after the administration, a level of a biomarker of pain sensation is statistically significantly decreased in the subject.

5. The method according to claim 4, wherein the biomarker is substance P.

6. The method according to claim 1, wherein after the administration, an electromyography signal is statistically significant decreased in the subject.

7. A method for treating visceral hypersensitivity in a subject in need thereof, comprising administering a composition, wherein the composition comprises an effective amount of *Lactobacillus plantarum* subsp. *plantarum* PS128 as the only active ingredient for treating the visceral hypersensitivity, which is deposited under DSMZ Accession No. DSM 28632, and a carrier, wherein the visceral hypersensitivity is associated with a functional gastrointestinal disorder selected from the group consisting of constipation and functional dyspepsia.

8. The method according to claim 7, wherein the functional gastrointestinal disorder is constipation.

9. The method according to claim 7, wherein the composition is orally administered to the subject.

10. The method according to claim 7, wherein after the administration, a level of a biomarker of pain sensation is statistically significantly decreased in the subject.

11. The method according to claim 10, wherein the biomarker is substance P.

12. The method according to claim 7, wherein after the administration, an electromyography signal is statistically significantly decreased in the subject.

13. A method for treating constipation in a subject in need thereof, comprising administering a composition, wherein the composition comprises an effective amount of *Lactobacillus plantarum* subsp. *plantarum* PS128 as the only active ingredient for treating constipation, which is deposited under DSMZ Accession No. DSM 28632, and a carrier.

14. The method according to claim 13, wherein the composition is orally administrated to the subject.

15. The method according to claim 13, wherein after the administration, a level of a biomarker of pain sensation is statistically significantly decreased in the subject.

16. The method according to claim 15, wherein the biomarker is substance P.

17. The method according to claim 13, wherein after the administration, an electromyography signal is statistically significantly decreased in the subject.

* * * * *

SEQUENCE LISTING

```
<160> NUMBER OF SEQ ID NOS: 2

<210> SEQ ID NO 1
<211> LENGTH: 22
<212> TYPE: DNA
<213> ORGANISM: Artificial
<220> FEATURE:
<223> OTHER INFORMATION: primer for ERIC-PCR
<220> FEATURE:
<221> NAME/KEY: misc_difference
<222> LOCATION: (1)..(22)

<400> SEQUENCE: 1
atgtaagctc ctggggattc ac                                        22

<210> SEQ ID NO 2
<211> LENGTH: 22
<212> TYPE: DNA
<213> ORGANISM: Artificial
<220> FEATURE:
<223> OTHER INFORMATION: primer for ERIC-PCR
<220> FEATURE:
<221> NAME/KEY: misc_difference
<222> LOCATION: (1)..(22)

<400> SEQUENCE: 2
aagtaagtga ctggggtgag cg                                        22
```